US009593325B2

United States Patent
Bendzko et al.

(10) Patent No.: US 9,593,325 B2
(45) Date of Patent: Mar. 14, 2017

(54) STABLE LYSIS BUFFER MIXTURE FOR EXTRACTING NUCLEIC ACIDS

(71) Applicants: Birgit Bendzko, Berlin (DE); Hans Joos, Berlin (DE)

(72) Inventors: Peter Bendzko, Berlin (DE); Hans Joos, Berlin (DE)

(73) Assignee: STRATEC BIOMEDICAL AG, Birkenfeld (DE)

( * ) Notice: Subject to any disclaimer, the term of this patent is extended or adjusted under 35 U.S.C. 154(b) by 240 days.

(21) Appl. No.: 14/171,157

(22) Filed: Feb. 3, 2014

(65) Prior Publication Data

US 2014/0154776 A1 Jun. 5, 2014

Related U.S. Application Data

(63) Continuation of application No. 12/988,906, filed as application No. PCT/DE2009/000549 on Apr. 20, 2009, now abandoned.

(30) Foreign Application Priority Data

Apr. 22, 2008 (DE) .......................... 10 2008 020 258

(51) Int. Cl.
*C12N 9/96* (2006.01)
*C12N 15/10* (2006.01)
*C12N 9/36* (2006.01)
*C12N 9/64* (2006.01)

(52) U.S. Cl.
CPC .............. *C12N 9/96* (2013.01); *C12N 9/2462* (2013.01); *C12N 9/6424* (2013.01); *C12N 15/1003* (2013.01); *C12N 15/1013* (2013.01); *C12N 15/1017* (2013.01)

(58) Field of Classification Search
None
See application file for complete search history.

(56) References Cited

U.S. PATENT DOCUMENTS

| | | | |
|---|---|---|---|
| 6,355,792 B1 | 3/2002 | Michelsen et al. | |
| 2003/0022231 A1* | 1/2003 | Wangh | C12Q 1/6806 435/6.11 |
| 2005/0014153 A1 | 1/2005 | Hlillebrand et al. | |
| 2006/0166233 A1 | 7/2006 | Wu et al. | |
| 2006/0223071 A1 | 10/2006 | Wisniewski et al. | |
| 2008/0014114 A1 | 1/2008 | Van Atta et al. | |

FOREIGN PATENT DOCUMENTS

| | | |
|---|---|---|
| DE | 102006019650 A1 | 10/2007 |
| EP | 1462520 A1 | 9/2004 |
| EP | 1529840 A1 | 5/2005 |
| WO | 03/040386 A2 | 5/2003 |

OTHER PUBLICATIONS

International Search Report for PCT/DE2009/000549 dated Nov. 12, 2009 (Form PCT/ISA/210) (German Translation).
International Search Report for PCT/DE2009/000549 dated Nov. 12, 2009 (Form PCT/ISA/210) (English Translation).
Qiagen RNAprotect Bacteria Reagent Handbook, Dec. 2005.
Yang et al, Langmuir 23:10533-10538 (2007).

* cited by examiner

*Primary Examiner* — Samuel Woolwine
(74) *Attorney, Agent, or Firm* — Buchanan Ingersoll & Rooney PC

(57) ABSTRACT

Embodiments relate to a lysis buffer mixture that is stable in storage for isolating nucleic acids from biological, preferably diagnostic samples. The mixture is preferably associated with an extraction control. The aim of the invention is to provide an improved nucleic acid extraction system, which is cost-effective, stable and easy to use, thus fulfilling the requirements of a modern nucleic acid extraction system and containing, among other things, extraction controls. Embodiments relate to a lysis buffer mixture for isolating nucleic acids, said mixture containing non chaotropic salts, a special selection of detergents, a defined quantity of at least one nucleic acid as an extraction control, optionally lytic enzymes, optionally carrier nucleic acids and optionally other additives.

19 Claims, No Drawings

STABLE LYSIS BUFFER MIXTURE FOR EXTRACTING NUCLEIC ACIDS

CROSS-REFERENCE TO RELATED APPLICATIONS

This application is a continuation of and claims priority to U.S. patent application Ser. No. 12/988,906, which was the United States National Phase under 35 U.S.C. §371 of PCT International Patent Application No. PCT/DE2009/000549, filed on Apr. 20, 2009, and claiming priority to German Patent Application No. 10 2008 020 258.4, filed on Apr. 22, 2008. Those applications are incorporated by reference herein.

BACKGROUND OF THE INVENTION

Field of the Invention

The invention relates to a storage-stable lysis buffer mixture for extraction of nucleic acids from biological, preferably diagnostic samples. It is preferably connected with an extraction control.

Fields of application are molecular biology diagnostics, research, medical practice, gene-based analysis of biotechnological, agricultural and foodstuff products as well as criminal science.

Background of the Related Art

A large number of customary lysis buffers for extraction of nucleic acids contain chaotropic ion mixtures as salts. The pertinent methods are based on a method developed and first described by Vogelstein and Gillespie (Proc. Natl. Acad. Sci. USA, 1979, 76, 615-619) for preparative and analytical cleansing of DNA fragments from agarose gels. The method combines the dissolution of the agarose containing the DNA bands to be isolated in a saturated solution of a chaotropic salt (NaJ) with a binding of the DNA to glass particles.

A method for isolation of nucleic acids practicable for a large number of varying applications has been shown in U.S. Pat. No. 5,234,809 (Boom). There a method for isolation of nucleic acids from initial substances containing nucleic acid by incubation of the initial substance with a chaotropic lysis buffer and a solid phase binding the DNA is described.

The chaotropic lysis buffers implement both the lysis of the initial substance as well as the binding of the nucleic acids to the solid phase.

However, lysis buffers of this kind also denaturate enzymes necessary for the lysis of a biological sample in a short period of time. This is why customary systems require a separate addition of the individual components. So the lysis buffer is only put together during the lysis procedure and the individual components are added in succession in accordance with a certain order.

The sequence of extraction and detection can be checked via various forms of control: the extraction control to determine the quality of the extraction and a reaction control to determine the quality of the detection method.

From patent application DE 19840531, solutions for stabilised process controls are known, although they are limited to stabilised (RT) qPCR controls in the corresponding reaction vessels. They are applied to the vessel surfaces in question free of water. In this way, an examination of the reverse transcriptase reaction and an examination of the qPCR reaction are made possible. However, the extraction remains uncontrolled in this context.

In the case of the extraction of very slight copy counts of nucleic acids, so-called carrier nucleic acids are often used, as slight quantities of nucleic acids are instable in an aqueous solution. These carrier nucleic acids may not have any kind of homology to the extracted nucleic acids and must normally be added separately in nucleic acid extraction systems. Typical carrier nucleic acids are salmon sperm DNA, herring sperm DNA, yeast t RNA and polyadenyl RNA.

In conventional methods, the carrier nucleic acids are customarily added to the sample in the extraction. This demands an additional pipetting step. The extraction control is also added to the sample in a known quantity in the extraction. This demands a further additional pipetting step. This results in difficulties in storing the control stably in a liquid form, to the extent that it comprises pure nucleic acids. Nucleic acids in low concentrations tend to degrade.

After this, the extraction control is measured, following the reaction, via a detection method, and the recovery rate can determined on the basis of the loss of control nucleic acid.

To counteract the effect of instability and also to simulate the extraction process, phage particles or nucleic acids packed in phage particles are sometimes used. However, production of such controls is very time-consuming and thus expensive.

The lytic enzymes are added to the reaction as liquid components in a further pipetting step. The reaction control for the detection methods is added to the detection reaction separately, which for its part demands an additional pipetting step, or the mixture for the detection reaction itself contains a so-called amplification control.

The following disadvantages result from this for the user:

All the components must be put together in various pipetting steps, which leads to additional work and the risk of contaminations.

The components of such a system have to be stored at differing temperatures. All told, automation of such a system proves to be complicated.

A different approach is shown in WO 0034463. Here, there is a description of a lysis buffer which is not based on chaotropic salts and suitable detergents.

As WO 0034463 shows, such mixtures are also storage-stable for some time as solid formulations. In WO 03040386, the possibility of the use of such a system for standardised nucleic acid extraction and for standardised detection of nucleic acid is described.

Publication WO 03040386 describes reaction areas which have the potential for efficient and fast methods. However, the manufacture of matching products is very time-consuming and bound to the later reaction area. The manufacture of the reaction areas in method WO 03040386 is via freeze-drying.

The reaction areas are provided with the various components of the reaction system in a water-free or practically water-free condition. This is connected with a lot of time being needed for weighing and taking the components to the reaction area and prevents automation to a great extent.

The carrier nucleic acids are put into the reaction area for the lysis buffer via the lysis vessel, often together with the extraction control. This is done via so-called coating methods, in which a solution of the nucleic acid mixture is dried onto the wall of the reaction vessel.

In order to complete the reaction mix for the lysis procedure, all that is now needed is a so-called lysis buffer mixture.

The lysis buffer mixture contains non-chaotropic salts and, if necessary, detergents and is prepared as a liquid mixture. This mixture is then dried. After drying, lytic enzymes in a solid form are added and the resulting powder mixed very thoroughly. The powder is then weighed and distributed to the coated reaction areas. In this way, there is a stable mixture for the lysis of samples containing nucleic acid in the reaction areas, this mixture being stable at room temperature for six months.

Separate addition of the enzymes as a dry substance is indispensable in this method, as the enzymes would partly denaturate in the mixture used during the drying.

The extraction control is also used as a reaction control for the detection method.

This method provides the following advantages for the user:

The sample can be added in a liquid form, no further pipetting steps are necessary and an enlargement of the volume of liquid samples is possible.

But the method also has disadvantages, which are in the manufacture and the shelf life:

Manufacture of the aforementioned system is very time-consuming, which makes the system expensive. The system merely has a shelf life of six months, in which context the coated vessels must be stored at −20° C., the coated vessels filled with lysis buffer mixture can then be stored at room temperature for six months.

To sum up, it can be stated that the user has a number of advantages in this procedure, but the manufacturing process becomes more complicated, with the result that the system is made more expensive in the long run.

BRIEF SUMMARY OF THE INVENTION

As a result of the increasing importance of the use of molecular biology methods in many areas, there is an increasing requirement for practical, favourably priced nucleic acid extraction systems which are simple and quick to use. In addition, extraction controls are becoming standards in molecular diagnostic applications with the modern qPCR detection methods.

However, keeping corresponding nucleic acids in suitable concentrations stable in solution is problematic.

The task underlying the invention is thus to provide an improved nucleic acid extraction system which is favourably priced, stable and simple to use, at the same time fulfilling the requirements of a modern nucleic acid extraction system by, inter alia, containing extraction controls.

DETAILED DESCRIPTION OF THE INVENTION

The object of the present invention is a lysis buffer mixture which can be manufactured liquid inclusive of all components for extraction of nucleic acids from biological, preferably diagnostic samples. It contains not only non-chaotropic salts to set the binding conditions for the solid phase separation, but also detergents for the lysis of the biological sample, a defined quantity of no less than one nucleic acid as extraction control, if necessary so-called carrier nucleic acids for the preparation of low concentrations of nucleic acid, if necessary enzymes for the lysis of the biological sample and possibly further additives.

The lysis buffer mixture is used for lysis of the samples via solid phase separation. It is put into a solid form by freeze-drying, thus resulting in a storage-stable formulation.

The focal point of the invention is the fact that the specific selection of detergents in combination with anti-chaotropic salts stabilises the enzymes used and the nucleic acids. It is surprising that the specific selection of detergents in the lysis buffer mixture makes it possible for all components to be put together in a liquid form. On the one hand, this leads to mutual stabilisation of the components and thus to an increased shelf life of the freeze-dried lysis buffer mixture (at least twice as long as conventional systems) and on the other hand to the manufacture of the mixture in question being independent of the reaction area.

The lysis buffer mixture can be produced in part steps (e.g. freeze-drying) in the reaction area, but also completely independently of this (e.g. in tablet form). Thus, the later reaction can be carried out in any imaginable reaction vessel.

In the invention, monovalent, bivalent or multivalent cations or mixtures of the cations are used as non-chaotropic salts.

Preferably, these cations are ammonium ions, sodium ions, potassium ions, magnesium ions, calcium ions, zinc ions or manganese ions.

Customarily, the lysis buffer mixture is obtained by two stem solutions being manufactured, mixed with one another, poured into reaction vessels and freeze-dried. Stem solution one preferably contains a mixture of one or more non-chaotropic salt(s), if necessary Tris, at least one detergent, at least one lytic enzyme. Stem solution two preferably contains the nucleic acid for extraction control, if necessary carrier nucleic acids, sugar and TrisHCl.

The quantity of non-chaotropic salts used depends on the salt in question or the mixtures. Preferably, the salts for the production of the lysis buffer mixture are used in concentrations of 5 mmol/l-3 mol/l. If ammonium chloride is used as a salt, it is used in a concentration between 1 and 2 mol/l, preferably in a concentration of 1.5 mol/l.

The pH value of the lysis buffer mixture is set between 5 and 9, a pH value of 8 being optimal.

As detergents, the lysis buffer mixture according to the invention contains cetyltrimethylammonium bromide (CTAB), Tween 20, Triton X-100 and/or sodium dodecyl sulfate (SDS), with CTAB preferably being contained.

The concentration of the detergents used for the lysis buffer mixture depends on the detergent and is in the range of 0.1-5%. In a preferred embodiment, CTAB in a concentration of 2% is used.

The lysis buffer mixture according to the invention contains nucleic acids for extraction control, which are synthetic nucleic acids or ones manufactured via molecular biology methods or also native nucleic acids. The nucleic acids can be DNA or RNA.

One or more DNA's, one or more RNA's or mixtures of one or more DNA's and RNA's can be used. The important thing is that the quantities of the nucleic acids for extraction control are known.

The extraction control nucleic acid is used for production of the lysis buffer mixture as a function of the later detection reaction, preferably in quantities of up to $10^{10}$ copies/ml.

The lytic enzymes contained in the lysis buffer mixture are preferably proteinases, muraminidases (e.g. lysozyme) and further enzymes for the degradation of bio-polymers. In a particular embodiment, proteinase K is used.

In a further particular embodiment, proteinase K and lysozyme are used.

In the invention, synthetic nucleic acids or isolates from biological materials are used as carrier nucleic acids. They can preferably be poly A RNA, tRNA, salmon sperm DNA or herring sperm DNA. Further ones are also possible.

The carrier nucleic acids are used for the production of the lysis buffer mixture in concentrations of 0.1 µg/ml to 100 µg/ml, optimally 10 µg/ml.

As further additive, the lysis buffer mixture possibly contains Tris, TrisHCl and also sugar, the sugar preferably being trehalose.

In a particular embodiment, the lysis buffer mixture according to the invention is available as a solid, storage-stable formulation in ready-to-use reaction vessels, ready for the lysis of samples containing nucleic acid. In the specific case of the embodiment, the reaction vessels are 2 ml micro-centrifuge vessels, although any kind of reaction vessel is imaginable for other applications, e.g. 96 well microtitre plates, 384 well microtiter plates as well as larger-volume vessels.

The invention further relates to a method for isolation of nucleic acids from any complex initial substances by making use of the lysis buffer mixture according to the invention.

In a particular embodiment, the method is used for isolation of DNA or RNA or DNA in combination with RNA from microorganisms.

The object of the invention is likewise a reaction kit for the extraction of nucleic acids.

In a preferred embodiment, the reaction kit contains vessels for sample lysis containing the lysis buffer mixture described here, possibly a binding buffer on an alcohol basis, possibly one or more washing buffer(s) known per se for cleansing of the nucleic acids as well as an elution buffer known per se. The nucleic acid is cleansed via solid phase adsorption on silicon surfaces or related surfaces. For this purpose, the kit contains spin filters or 96 well filter plates or magnetic beads with the corresponding surfaces.

In an embodiment of the invention, the reaction kit is suited to the extraction of viral nucleic acids from diagnostic samples.

Likewise, the reaction kit is suited to the extraction of bacterial nucleic acids from diagnostic samples in a further embodiment.

In a particular variant of an embodiment of the invention, the kit contains a 2 ml lysis vessel with the mixture, a binding buffer on an isopropyl alcohol basis, two different washing buffers, known per se, an elution buffer known per se as well as spin filters as the adsorption phase. This kit is particularly suited to isolation of viral nucleic acids from diagnostic samples.

The invention has the advantage that the manufacture of the lysis buffer formulation does not depend on the reaction area. The mixture can be produced both in the reaction room and also independent of it.

The extraction control nucleic acids are stabilised in a stabilisation solution (stem solution two), which is added to the lysis buffer mixture (stem solution one). With the lysis buffer mixture which results, vessels are filled. This fluid mixture of all the components and, if necessary, an aliquot makes an automated manufacturing process for the formulation possible.

The contents of the vessels are freeze-dried.

The extraction control is also used thereafter as a reaction control for the detection method.

In a particular embodiment, the lysis buffer mixture can be manufactured in a tablet form. These tablets are then later added to the sample to be lysed.

After freeze-drying, the components remain stable and protect one another against any possible degradation. As a result of their hygroscopy, the salt components trap liquid from the atmosphere up to a certain extent and thus protect the enzymes and the nucleic acids. Naturally, it is not the individual components of the mixture alone which cause the stabilisation, but also the coordinated quantities of the ingredients in question. In the quantities, one must consider that the corresponding mixture must be suited as a component in a solid phase separation for nucleic acids.

Surprisingly, the lysis buffer mixture in accordance with the invention has a shelf-life of at least one year at room temperature. As opposed to this, the shelf-life of lysis buffer mixtures described in the state of the art up to now is a maximum of six months, partly with refrigeration.

An advantage of the present embodiment of the invention is explained below by means of a comparison of the sequence of the lysis procedure for the nuclide acid extraction.

A conventional lysis starts with a sample, to which liquid lysis buffer containing salt is added with detergents, the volume is adjusted with water, and then, in individual steps, the enzymes, the control nucleic acids and, if necessary, the carrier nucleic acids are added. Only then can the lysis procedure take place.

On the other hand, a lysis making use of the invention is quite simple as follows: the sample is put into a pre-filled vessel with the ready-to-use mixture and the volume is adjusted with water, the lysis procedure takes place.

As in WO 03040386, the basis of this invention is a lysis buffer based on non-chaotropic salts and suitable detergents.

Unlike the procedure from WO 03040386, manufacture here does not depend on the reaction area.

A further advantage, alongside the speed already described as a result of the lack of a number of additional steps, is a reduced risk of contamination.

The invention enables both automated manufacture of the reaction unit for the lysis step with the manufacturer and also simplification of the automated extraction with the user, as a number of liquid handling steps with small volumes are no longer necessary (addition of enzymes, carrier nucleic acids and controls).

An additional advantage is the enlargement of the possible sample volume, a liquid mixture contains water per se, liquid diagnostic samples (body fluids and excretions) can be added in a larger volume. This increases the quantity of isolated nucleic acids and thus the sensitivity of corresponding pathogen detections.

In this way, this lysis buffer mixture also fulfils modern demands made of a concentrated lysis buffer.

An advantage of the present invention for the manufacture of corresponding systems can be portrayed as follows.

The manufacture of the lysis buffer mixture described here is simple, as a stabilised lysis buffer mixture is used, in which all the components are available together in an aqueous solution.

The solution is portioned mechanically in reaction vessels and then freeze-dried. This procedure is favourable as regards costs.

To carry out the test, the sample can be added to the lysis buffer mixture in one step. Manufacture of the lysis buffer mixture in a tablet form is also possible. In this way, the lysis buffer mixture can also be added to the sample directly as a tablet.

The lysis buffer mixture has a shelf life of at least 12 months at room temperature. Thus, storage of this mixture without refrigeration is also possible.

The sample can be added in a liquid form, no further pipetting steps are necessary, by which the risk of contamination for the sample as a result of cross-contamination and also for the user as a result of infectious samples is reduced.

An enlargement of the volume of liquid samples to be used is possible, which also has the effect of increased sensitivity of the detection procedure.

Below, the invention is explained in more detail on the basis of the embodiments.

EMBODIMENT 1

Production of a Mixture According to the Invention Described Here for the Lysis of Diagnostic Samples Containing Bacteria A solution I of 1.5 M ammonium chloride, 10 mM Tris pH 8, 2% CTAB, 0.5 mg proteinase K/ml and 0.5 mg lysozyme/ml is produced.

A solution II of 600 µg/ml polyadenyl RNA, $10^7$ copies/ml control DNA fragment plasmid pCONT, 1% trehalose and 50 mM TrisCl, pH 8, is produced. Solutions I and II are mixed in a ratio of 40:1.

The solution is frozen in 400 µl portions in closable 2 ml reaction vessels. Then, these vessels are freeze-dried with the contents and are referred to as extraction tubes bacteria in the further text.

EMBODIMENT 2

Production of a Mixture According to the Invention Described Here for the Lysis of Diagnostic Samples Containing Viruses A solution I of 1.5 M ammonium chloride, 10 mM Tris pH 8, 2% CTAB, 0.5 mg proteinase K/ml and 0.5 mg lysozyme/ml is produced.

A solution II of 600 µg/ml polyadenyl RNA, $10^7$ copies/ml control DNA fragment plasmid pCONT, $10^8$ copies/ml control RNA fragment, 1% trehalose and 50 mM TrisCl, pH 8, is produced.

Solutions I and II are mixed in a ratio of 40:1.

The solution is frozen in 400 µl portions in closable 2 ml reaction vessels. Then, these vessels are freeze-dried with the contents and are referred to as extraction tubes virus in the further text.

EMBODIMENT 3

Standardised Extraction of Viral RNA (Influenza A Virus) and Viral DNA (HBV) by Means of the Produced Lysis Mixture Via Spin Filters Serum samples (200 µl) with the corresponding viruses in a known number of copies (HBV 500 copies per preparation) or with an estimated titre quantity (Influenza A Virus) are used for extraction.

200 µl serum and 200 µl water are poured into an extraction tube virus with the mixture for virus lysis and there is thorough mixing. There is then incubation for 15 min at 65° C. in an Eppendorf thermo-mixer under continuous shaking, then incubation for 10 min at 95° C. in the Eppendorf thermo-mixer. 400 µl of isopropyl alcohol is added, followed by mixing by means of repeated pipetting up and down The lysate is placed on a spin filter of the firm of Invitek and incubated for one minute at room temperature. After this, it is centrifuged for one minute at 10,000 rpm in an Eppendorf table-top centrifuge. The spin filter is washed twice with a washing buffer comprising 10 mM Tris pH 8, 70% ethanol. The spin filter is centrifuged dry for five minutes. There is elution with 100 µl RNase/DNase free water, with preliminary incubation for three minutes and then centrifuging.

The viruses and the extraction control are detected via quantitative PCR systems.

For *Bacillus subtilis* a control reaction put together by Invitek is used via SYBR green dyeing. For the detection of the DNA extraction control, a system of the firm of Invitek is used (DNA Control Detection Assay or via quantitative reverse transcriptase PCR systems.

For Influenza A and HBV, detection systems of the firm of Congen are used (Avian Influenza A, Hepatitis B Virus). For the detection DNA and RNA extraction controls, systems of the firm of Invitek are used (DNA Control Detection Assay, RNA Control Detection Assay).

5 µl of eluate are used as a template and the procedures are carried out on a Rotorgene 3000 device of the firm of Corbett according to the manuals provided.

EMBODIMENT 4

Standardised Extraction of Viral RNA (Influenza A Virus) and Viral DNA (HBV) by Means of the Produced Lysis Mixture Via Silicon Magnetic Particles Serum samples (200 µl) with the corresponding viruses in a known number of copies (HBV 500 copies per preparation) or with an estimated titre quantity (Influenza A Virus) are used for extraction.

200 µl serum and 200 µl water are poured into an extraction tube virus with the mixture for virus lysis and there is thorough mixing. There is then incubation for 15 min at 65° C. in an Eppendorf thermo-mixer under continuous shaking, then incubation for 10 min at 95° C. in the Eppendorf thermo-mixer. 400 µl of isopropyl alcohol is added, followed by mixing by means of repeated pipetting up and down. 20 µl MAP A Solution of the firm of Invitek are added to the solution followed by incubation for five minutes at room temperature. During this, the magnetic particles are mixed by a magnetic separator, KingFisher mL, of the firm of Thermo. Then, the magnetic particles are washed in two successive cavities with the washing buffer comprising 10 mM Tris pH 8, 70% ethanol.

The magnetic particles are then dried for 10 minutes at room temperature to remove the alcohol.

There is elution with 100 µl RNase/DNase free water in a further cavity, with mixture for three minutes and then separation of the magnetic particles.

The viruses and the extraction controls are detected via quantitative PCR systems or via quantitative reverse tranreverse transcriptase PCR systems.

For Influenza A and HBV, detection systems of the firm of Congen are used (Avian Influenza A, Hepatitis B Virus). For the detection DNA and RNA extraction controls, systems of the firm of Invitek are used (DNA Control Detection Assay, RNA Control Detection Assay).

5 µl of eluate are used as a template and the procedures are carried out on a Rotorgene 3000 device of the firm of Corbett according to the manuals provided.

EMBODIMENT 5

Standardised Extraction of Bacterial DNA (*Bacillus subtilis*) by Means of the Produced Lysis Mixture Via Spin Filters Sample bacteria pellets from various quantities of culture of *Bacillus subtilis* are used for extraction.

The bacteria from the pellets are put into an extraction tube with the mixture for bacteria lysis together with 400 μl water and there is thorough mixing. There is incubation for 20 min at 37° C. in an Eppendorf thermo-mixer under continuous shaking, then incubation for 15 min at 65° C. in the Eppendorf thermo-mixer, with incubation for 10 min at 95° C. in the Eppendorf thermo-mixer as the final step. 400 μl of isopropyl alcohol is added, followed by mixing by means of repeated pipetting up and down. The lysate is placed on a spin filter of the firm of Invitek and incubated for one minute at room temperature. After this, it is centrifuged for one minute at 10,000 rpm in an Eppendorf table-top centrifuge.

The spin filter is washed twice with a washing buffer comprising 10 mM Tris pH 8, 70% ethanol. The spin filter is centrifuged dry for five minutes. There is elution with 100 μl RNase/Dnase free water, with preliminary incubation for three minutes and then centrifuging.

The bacteria and the extractions control are detected via quantitative PCR systems.

For *Bacillus subtilis* a control reaction put together by Invitek is used via SYBR green dyeing. For the detection of the DNA extraction control, a system of the firm of Invitek is used (DNA Control Detection Assay).

5 μl of eluate are used as a template and the procedures are carried out on a Rotorgene 3000 device of the firm of Corbett according to the manuals provided and the laboratory directive for *Bacillus subtilis*.

EMBODIMENT 6

Standardised Extraction of Bacterial DNA (*Bacillus subtilis*) by Means of the Produced Lysis Mixture Via Silicon Magnetic Particles Sample bacteria pellets from various quantities of culture of *Bacillus subtilis* are used for extraction.

The bacteria from the pellets are put into an extraction tube with the mixture for bacteria lysis together with 400 μl water and there is thorough mixing. There is incubation for 20 min at 37° C. in an Eppendorf thermo-mixer under continuous shaking, then incubation for 15 min at 65° C. in the Eppendorf thermo-mixer, with incubation for 10 min at 95° C. in the Eppendorf thermo-mixer as the final step. 400 μl of isopropyl alcohol is added, followed by mixing by means of repeated pipetting up and down. The lysate is placed on a spin filter of the firm of Invitek and incubated for one minute at room temperature. 20 μl MAP A Solution of the firm of Invitek are added to the solution followed by incubation for five minutes at room temperature. During this, the magnetic particles are mixed by a magnetic separator, KingFisher mL, of the firm of Thermo. Then, the magnetic particles are washed in two successive cavities with the washing buffer comprising 10 mM Tris pH 8, 70% ethanol. The magnetic particles are then dried for 10 minutes at room temperature to remove the alcohol.

There is elution with 100 μl RNase/Dnase free water in a further cavity, with mixing for three minutes and then separation of the magnetic particles. The bacteria and the extractions control are detected via quantitative PCR systems.

For *Bacillus subtilis* a control reaction put together by Invitek is used via SYBR green dyeing, which is not to be published here. For the detection of the DNA extraction control, a system of the firm of Invitek is used (DNA Control Detection Assay).

5 μl of eluate are used as a template and the procedures are carried out on a Rotorgene 3000 device of the firm of Corbett according to the manuals provided and the laboratory directive for *Bacillus subtilis*.

We claim:

1. A method for preparing storage-stable, freeze-dried lysis buffer mixture for the isolation of nucleic acids from arbitrary complex initial substances, wherein said method comprises individual preparation of a first aqueous stem solution and a second aqueous stem solution, which are then mixed with one another, followed by mechanically portioning and freeze drying, wherein said first aqueous stem solution contains a mixture of at least one non-chaotropic salt, Tris, at least one detergent and at least one lytic enzyme, and wherein said second aqueous stem solution contains a nucleic acid for extraction control, carrier nucleic acids, sugar, and Tris-HCl.

2. The method of preparing the lysis buffer mixture of claim 1, wherein the non-chaotropic salts of said first aqueous stem solution contain cations selected from the group consisting of monovalent cations, bivalent cations, multivalent cations, and mixtures thereof.

3. The method of preparing the lysis buffer mixture of claim 2 wherein the cations are selected from the group consisting of ammonium ions, sodium ions, potassium ions, magnesium ions, calcium ions, zinc ions and manganese ions.

4. The method of preparing the lysis buffer mixture of claim 1, wherein the pH value of the lysis buffer mixture is set between 5 and 9 when in aqueous solution prior to being freeze-dried.

5. The method of preparing the lysis buffer mixture of claim 1 wherein the at least one detergent of said first aqueous stem solution is selected from the group consisting of cetyltrimethylammonium bromide, Tween 20, Triton X-100, and sodium dodecyl sulfate.

6. The method of preparing the lysis buffer mixture of claim 1, wherein the at least one detergent of said first aqueous stem solution is cetyltrimethylammonium bromide.

7. The method of preparing the lysis buffer mixture of claim 1, wherein the at least one detergent of said first aqueous stem solution is present in the range of 0.1-5% of the total quantity.

8. The method of preparing the lysis buffer mixture of claim 1, wherein cetyltrimethylammonium bromide (CTAB) of said first aqueous stem solution is present as 2% of the total quantity.

9. The method of preparing the lysis buffer mixture of claim 1, wherein the defined quantity of at least one nucleic acid as an extraction control of said second aqueous stem solution is selected from the group consisting of a synthetic nucleic acid, a nucleic acid manufactured via molecular biology methods, and a native nucleic acid.

10. The method of preparing the lysis buffer mixture of claim 1, wherein the defined quantity of at least one nucleic acid for extraction control of said second aqueous stem solution is selected from the group consisting of at least one DNA, at least one RNA, and mixtures of at least one DNA and at least one RNA.

11. The method of preparing the lysis buffer mixture of claim 1, wherein the at least one lytic enzymes of said first aqueous stem solution are proteinases.

12. The method of preparing the lysis buffer mixture of claim 1, wherein the at least one lytic enzymes of said first aqueous stem solution are proteinase K.

13. The method of preparing the lysis buffer mixture of claim 1, comprising lytic enzymes, wherein the at least one lytic enzymes of said first aqueous stem solution are proteinase K and lysozyme.

14. The method of preparing the lysis buffer mixture of claim 1, wherein the carrier nucleic acids of said second aqueous stem solution are synthetic nucleic acids or isolates from biological materials.

15. The method of preparing the lysis buffer mixture of claim 1, wherein the carrier nucleic acids of said second aqueous stem solution are poly A RNA, tRNA, salmon sperm DNA, or herring sperm DNA.

16. The method of preparing the lysis buffer mixture of claim 1, wherein the lysis buffer mixture is prepared as a solid, storage-stable formulation in ready-to-use reaction vessels.

17. The method of preparing the lysis buffer mixture of claim 16, wherein the ready-to-use reaction vessels are 96 well microtitre plates, 384 well microtitre plates, or 0.5-5 ml reaction vessels.

18. The method of preparing the lysis buffer mixture of claim 16, wherein the ready-to-use reaction vessels are 2 ml reaction vessels.

19. The method of preparing the lysis buffer mixture of claim 1, wherein the lysis buffer mixture is prepared in a tablet form.

* * * * *